(12) United States Patent
Postrekhin et al.

(10) Patent No.: US 10,821,294 B2
(45) Date of Patent: Nov. 3, 2020

(54) MAGNETIC FIELD OPTIMIZATION METHOD AND DEVICE FOR BLOOD FLOW MICROCIRCULATION ENHANCEMENT

(71) Applicants: Yevgeniy Postrekhin, Orlando, FL (US); Catherine Zelner, Windermere, FL (US); Pavel Marchenko, Orlando, FL (US)

(72) Inventors: Yevgeniy Postrekhin, Orlando, FL (US); Catherine Zelner, Windermere, FL (US); Pavel Marchenko, Orlando, FL (US)

(*) Notice: Subject to any disclaimer, the term of this patent is extended or adjusted under 35 U.S.C. 154(b) by 289 days.

(21) Appl. No.: 15/910,189

(22) Filed: Mar. 2, 2018

(65) Prior Publication Data

US 2019/0269932 A1 Sep. 5, 2019

(51) Int. Cl.
*A61N 2/02* (2006.01)
*A61B 5/0265* (2006.01)
*A61B 5/024* (2006.01)
*A61B 5/05* (2006.01)

(52) U.S. Cl.
CPC ............... *A61N 2/02* (2013.01); *A61B 5/024* (2013.01); *A61B 5/0265* (2013.01); *A61B 5/05* (2013.01)

(58) Field of Classification Search
CPC .......................... A61N 2/00–12; A61B 5/0265
See application file for complete search history.

(56) References Cited

U.S. PATENT DOCUMENTS

| | | | | |
|---|---|---|---|---|
| 5,269,747 A | * | 12/1993 | Erickson | A61N 2/02 600/14 |
| 2010/0057146 A1 | * | 3/2010 | Gleim | A61N 2/02 607/1 |
| 2017/0136242 A1 | * | 5/2017 | Durand | G05B 19/042 |

* cited by examiner

*Primary Examiner* — Thaddeus B Cox

(57) ABSTRACT

The present invention provides an apparatus and method to increase blood microcirculation in tissue, using the pairs of Helmholtz coils with different frequencies; shape and amplitude of the magnetic field were built covering this tissue. A Giant Magnetoresistance Sensor or Laser Doppler flow meter sensor is used to determine a feedback from the tissue where the magnetic field is applied. The method includes calibration of the sensors and a special time protocol for the magnetic field to identify the maximum field effect for increasing blood microcirculation. This device includes the Helmholtz coils to apply the alternating magnetic field, a giant magnetoresistance sensor to measure feedback after applying the alternating magnetic field, a power amplifier for the Helmholtz coils and the giant magnetoresistance sensor, a data acquisition box, a virtual function generator and a virtual oscilloscope all of which are connected to communicate with a computer.

14 Claims, 5 Drawing Sheets

MAGNETIC FIELD OPTIMIZATION METHOD AND DEVICE FOR BLOOD FLOW MICROCIRCULATION ENHANCEMENT

FIELD OF THE INVENTION

The present invention relates generally to method and device for therapeutic application of magnetic fields, and, more particularly, to a method and device for optimization of the blood microcirculation for targeted parts of the human body using feedback from a giant magnetoresistance sensor or similar sensor to sense the blood microcirculation and trigger bioelectromagnetic resonance.

BACKGROUND

U.S. Pat. No. 5,131,904 describes process which involves treating organs by applying a magnetic field by means of an annular coil surrounding the organ. The coil being energized by a pure DC voltage having a rectangular wave form pulsing at the rate of 1-30 CPS. The therapy carried out by means of such an apparatus is now known as PST (pulsed signal therapy). The invention also includes an apparatus comprising a body support encompassed by an annular coil energized as above. The coil is mounted on a carriage running on tracks adjacent the body support. The patent also acknowledges that the intrinsic magnetic field strength of living individuals possess measurable amounts of a magnetic field (MF). The data further indicates that most healthy people have a MF which ranges from X to Y gauss. Some human beings have extremely low MF levels: other human beings have extremely high MF levels, i.e. 4 to 5 times (X+Y/2).

U.S. Pat. No. 7,588,529 discloses a similar pulsed signal therapy device wherein the patient places the body part to be treated inside a cylindrical coil in which pulse signals are generated. The intensity and frequency of these pulsed signals are varied according to a predetermined biological pattern, depending on what kind of disease or condition is to be treated. The pulsed signals have a relatively low frequency and energy. To assist the proper positioning of the body part inside the coil, a shapeable pillow may be provided with this apparatus. The voltage supplied repeatedly builds up steeply, holds, and then deteriorates steeply so that there is created a series of spaced working plateaus p of pure DC current. It is preferred, therefore, that in the duty cycle the wave form of the pure DC voltage will be virtually of a rectangular shape with the abruptly rising r and abruptly falling d sides of the wave form comprising sides of a rectangle. In between two such duty cycles there is an off cycle.

U.S. Pat. No. 5,993,375 patent discloses the use of a modular magnetic pad having permanent magnets for magnetic therapy. The pad has one planar surface with a perimeter of a fastening material and an opposing planar surface of a mating fastening material. The fastening material may be a hook-type fastener and the mating fastening material may be a loop-type fastening material. One such fastening material is commonly known as a VELCRO fastener. This pad structure permits a plurality of pads to be fastened together in any desired configuration by attaching the fastener material on one surface to the mating fastener material on the other surface. A wrap may be used to hold the attached pads adjacent any desired portion of the body requiring treatment.

U.S. Pat. No. 6,234,953 gives an apparatus and method for magnetic treatment of a disorder selected from the group of physiological, neurological and behavioral disorders. The method comprises applying a specific low frequency pulsed magnetic field having a plurality of intermittent waveforms to a subject, for a time effective to produce a desired effect in a target tissue. A multi-functional, modular pulse electromagnetic field biophysical stimulation field generator device and healing system is disclosed. The device discloses using small coils and a pulse electromagnetic field technique for treatment of a variety of conditions to achieve an anticipated shorter healing and rehabilitation time. An activation signal having a combined waveform is used to activate the coils, comprising a high frequency carrier wave, which is amplitude-modulated, by a low frequency treatment wave for optimal penetration of biological tissue. The coils are arranged to insure maximum focusing of the energy to the treatment site. Minimization of the undesired effects of electromagnetic fields on living tissue is achieved by using the small magnetizing coils, thereby preventing electromagnetic field dispersion to adjacent tissues.

U.S. Pat. No. 6,955,642 discloses a noninvasive method and apparatus for treating living tissue with pulsed electromagnetic fields (PEMFs) having selectively reduced high-frequency signal components. The improved bioresponse is disclosed as being provided by magnetic field amplitudes less than approximately 40 uT, and most preferably in the range of 4-10 uT. Such amplitude levels for the disclosed PEMF signal are disclosed as being particularly effective with a treatment duration in the range of 0.25 to 2 hours/day.

U.S. Pat. No. 7,175,587 discloses an apparatus and method for pulsed applying electromagnetic therapy to humans and animals. A straight wire element is employed to generate the magnetic field. A power and timer circuit supply current pulses, that approximate square pulses in form, so that the straight wire element generates magnetic pulses having rapid rise and fall times. The peak field strength is approximately 2 gauss at a 1 cm distance from the straight wire element, and the duration of peak field strength is approximately 200 nanoseconds. The pulses are repeated at a frequency of about 70 HZ. The straight wire element and circuit may be housed in a hand-held probe, with an LED illuminating the skin area to provide a visual indication of active range, or a plurality of the straight wire elements and associated circuits may be embedded in a conformable pad that is placed over the treated area of the body.

U.S. Pat. No. 8,216,121 discloses a device for generating a pulsed electromagnetic field with pulse control, wherein the pulses provided by the pulse generator represent periodic pulses having ascending and descending envelope curves with a harmonic or anharmonic oscillation profile within the envelope curves. The pulse sequence is in the range of from 1 pulse/20 minutes to 10 pulses/minute, with pulse sequence, pulse function type and electromagnetic flux density being controlled via values which are obtained using non-invasive measuring methods on a target tissue. These values represent features of the blood microcirculation, with exponential functions as such as pulse function type being excluded. The EF pulses disclosed in this patent are directed to the skin surface of the patient.

U.S. Pat. No. 8,180,427 discloses an apparatus and method for non-invasively sensing pulse rate and blood flow anomalies using a localized, uni-directional, and constant magnetic field. The apparatus comprises a magnetic source for producing the magnetic field, a signal acquisition module with a magnetic sensor for detecting the modulations of the magnetic field caused by the blood flow; and a signal processing module for processing the acquired signals to produce data relating to pulse rate and blood flow anomalies.

The method senses pulse rate and blood flow anomalies by providing a localized, uni-directional, and constant magnetic field in proximity to a blood vessel; detecting the variations of the magnetic field caused by the flow of pulsatile blood within the blood vessel and processing the signals of the detected variations to monitor the blood flow.

Based on medicals trials and scientific evidence on the influence EMF on the human body, numerous electromagnetic devices are commercially available. The commercially available devices exploit different combinations of rectangular electromagnetic pulses or sinusoidal signals to provide the desire effect on parts of human body. One commercially available device is the SEQEX device manufactured by S.I.S.T.E.M.I.S.r.l. of Italy. This device is described as an advanced electro medical device developed to provide an Ion Cyclotron Resonance (ICR) therapy. It operates using specific magnetic fields that vary in intensity, frequency, and form and more particularly a device that generates pulsed low frequency electromagnetic fields capable of inducing extremely low intensity wave. The BEMER-3000 is a commercially available pulsed electromagnetic device manufactured by Beemer AG of Triesen, Liechtenstein. This device is designed for improving blood microcirculation. This device induces magnetic field with special pulsed wave form: sinusoidal plus single pulses with intensity of the magnetic field from 10 to 35 micro Tesla. Based on a medical trial published by the creators of this device, the microcirculation of blood vessels may be improved using the pulsed wave form.

The above patents and devices disclose features or advantages using different types of the application of magnetic fields with different type of pulses, frequencies, amplitudes. These devices and methods claim to produce a positive effect on the human body. Despite this, none of the references give an active indication of how good the effect is or how to optimize the positive effect of the magnetic field. It is entirely possible, depending on the skill of the user, the patient may receive a harmful dose or ineffective amount of therapy to the target tissue. The present invention optimizes the effect of the magnetic field acting on the human body using feedback from sensors which measure the response based on the blood microcirculation of the patient. The present invention is based on the approach of the human tissue as a colony of bio cells with certain electrochemical and electromagnetic properties. The preferred approach is to determine the bioelectromagnetic resonance by applying the electromagnetic field such that a small induced current produces a large flow ion current inside the bio-cells resulting in increased metabolism and increased blood microcirculation in the target tissue of the patient.

SUMMARY OF INVENTION

In the present invention, a triangular shaped electromagnetic field is used to add additional induced current to the cells of the target tissue of a patient. This involves the flow of positive and negative ions through the cell membrane. Different organs have different types of cells with different characteristics such as size, capacitance and electroconductivity. Each patient has a specific size, capacitance and conductivity for their own cells in the target tissue. The present invention initiates bioelectromagnetic resonance in the target tissue of a patient by applying a small triangular external electromagnetic field to the target tissue. The small induced current then produces a large flow current inside the cells. Once this optimal current for the target tissue is determined, the electromagnetic field at the desired applied current is applied to increase the cell metabolism and blood microcirculation in the target tissue.

To increase blood microcirculation in tissue, a pair of Helmholtz coils were built to enclose or surround the tissue to be treated. A Helmholtz coil is a device for producing a region of nearly uniform magnetic field. It consists of two solenoid electromagnets on the same axis. A Helmholtz pair consists of two identical circular magnetic coils (solenoids) that are placed symmetrically along a common axis, one on each side of the target area, and separated by a distance h equal to the radius R of the coil to simplify the geometrical factor of the coils.

A triangle shape alternating magnetic field at the target tissue is created with the coil current from about 0.1 A to 1 A and frequency from about 18 Hz to 38 Hz is applied to the Helmholtz coils to optimize the blood microcirculation. A Giant Magnetoresistance Sensor (GMS) is used to determine feedback from the target tissue where the magnetic field is applied. This approach is based on the principles of Giant Magnetoresistance (GMR) which is related to the large change in the electrical resistance that is induced by the application of a magnetic field to thin films composed of alternating ferromagnetic and nonmagnetic layers. A procedure for determining the optimal range of the magnetic field is then processed to find the "personal resonance conditions" or bioelectromagnetic resonance of the target cells of a patient to optimize the metabolism and blood microcirculation. The data collected is then used to tailor the applied magnetic field to optimize the treatment for the patient using the individualized bioelectromagnetic resonance.

This procedure includes an initial calibration step. A pressure cuff is attached to the arm, and the feedback sensors GMS and a laser Doppler sensor (LDS) are positioned along the appropriate area of the arm to control and sense blood microcirculation. The data from the sensors at zero external magnetic field are then recorded. The user then increases the pressure in the cuff up to 200 mm Hg. This pressure is kept for approximately two minutes. The pressure in the cuff is then reduced slowly at the same time as data from the sensors are recorded to reflect the increase or decrease in the blood microcirculation in the body part to be treated.

The second step is to determine the time protocol for the external magnetic field. The target part of the human body, for example palm of the patient, is positioned between the Helmholtz coils and the feedback sensors GMS and LDS are attached to appropriate area of the arm to control blood microcirculation and to read the data from sensors. The magnetic coils are then used to apply current from the magnetic coils with the triangle shape at predetermined frequency and amplitude of about 0.1 A to the target tissue. The current is applied for approximately two minutes and the magnetic field is then reduced to zero. During this time, zero magnetic field is applied to the target tissue and during this period, the data from the sensors is read to detect any remainder voltage. Next, a coil current of about 0.2 A is applied to the coil for another 2 minutes. The current is then reduced to zero and kept at zero current for two minutes at the same time as data is collected from the sensors. This sequence is continued at increasing 0.1 A intervals. This time protocol is performed for any amplitude and frequency to determine the optimal magnetic field to be used for the preferred blood microcirculation. The similar time protocol may be done for any frequency and amplitude of the magnetic field depending on the area of the patient to be treated. Once the desired frequencies and amplitudes are completed, the optimum frequency and amplitude of the magnetic field may be determined based on the detected feedback from the sensor responses. The application of the optimal frequency and amplitude will effectively increase the metabolism of the target cells and blood microcirculation to provide an improved response to treatment at the target tissue for the individual patient.

To identify the optimal blood microcirculation, the device is built for sensing the blood microcirculation in the body part that is to be treated. This device includes the Helmholtz coils to apply the alternating magnetic field, the giant magnetoresistance sensor to measure feedback after applying the alternating magnetic field, a power amplifier for the Helmholtz coils, the amplifier for the giant magnetoresistance sensor, a data acquisition box, a virtual function generator and virtual oscilloscope which are connected and controlled by the computer.

DETAILED DESCRIPTION

Figure 1:
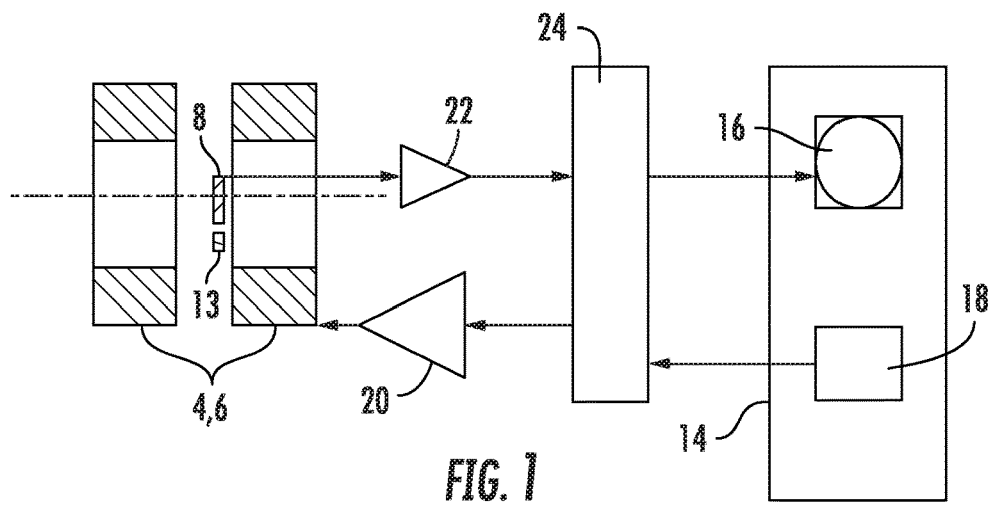
FIG. 1 is a Block-diagram of the device to measure the feedback of the blood microcirculation.

The positive influence of an electromagnetic field (EMF) on the living cells is generally known. Many medical centers have shown how alternating EMF acting on different parts of the human body may provide improved clinical results. The present invention is directed to improving the blood flow of the target tissue at the micro-vascular level. The periodic contraction and relaxation of the vessel wall originates from the intrinsic ability of smooth muscle cells to become periodically polarized and depolarized. Synchronized oscillations in cell activity are seen in many cell types. In the vascular wall, synchronized oscillations of smooth muscle cell tension give rise to oscillations of vascular tone (vasomotion), which are of physiological and pathophysiological importance. Vasomotion is known to be associated with slow oscillations of smooth muscle membrane potential and of intracellular Ca concentration. It has also been demonstrated that the function of the sarcoplasmic reticulum (SR) is critically important for the activity, whereas potassium channels play only a modulatory role. The role of the endothelium differs between vascular beds. In some, a functional endothelium is essential for vasomotion, whereas in others, vasomotion is promoted after removal of the endothelium.

At the micro-vascular level, there are different concentration of ions like calcium Ca+, potassium K+, sodium Na+, chlorine Cl−, organic complex A− inside and outside of the membrane cell. This difference creates diffusion flux of these ions through the cell membrane. Any diffusion process goes toward equilibrium. The bilayer cell membrane of the micro vasculature has special active channels through which ions can be pumped against the diffusion flow of ions. This process needs energy which is delivered to the cell by ATP molecules. Part of this mechanism includes microcirculation of blood to supply nutrition and oxygen to the cells. The microcirculation is directly related to vasomotion of blood vessels. This is a mechanical contraction of vessels with very low frequency from about 0.001 to 0.1 Hz. From several scientific sources it is known that the vasomotion is directly related to the oscillation of calcium ions Ca+ concentration inside living cells. The mechanism of moving ions (K+, Na+, Ca+, Cl−) in and out of the cell has been experimentally confirmed and described in detail in various references.

The moving flux of ions creates an electrical current and the cell membrane can be presented as an electrical circuit with conductance (resistance) g for every pumped ion, the cell membrane is a capacitor C with equilibrium potential E, active channels of ion presented as generator with voltage V. All cells actively maintain a difference in electrical charge across their membrane. This difference in charge gives rise to a voltage difference, or potential. In most cell types the steady-state membrane potential is called resting potential. Cells employ ion pumps to maintain gradients of ion concentrations across their membranes. The present invention considers the steady-state potential that arises from these ion gradients. For example, if outside membrane cell concentration of positive ion is $[K+]_e$, inside membrane cell concentration is $[K+]_i$, the system will reach a steady state in which an electrically-driven inward transport rate balances the outward diffusion rate. The voltage difference at this equilibrium state is called the Nernst potential and is given in volts $$E_k = (RT/zF)\text{Ln}([K+]_e/[K+]_i) \quad (1)$$

Where R is ideal gas constant, T is temperature in degrees Kelvin, z is the charge of the migrating ion (its valence), and F is Faraday's constant. It is known concentrations of ions in mammalian skeletal muscle is given in Table 1

TABLE 1

| ion | Intracellular (mM) | Extracellular (mM) |
|---|---|---|
| Na+ | 12 | 145 |
| K+ | 155 | 4 |
| Ca 2+ | 10-4 | 1.5 |

And it is easy to find Eka, Ena, Eca, constancies are R=8.315 (J/mol K), F=9.648*10^4 C/mol, T=310.10 K (37 C), so RT/F=26.7*10^−3 J/C (Joule per Coulomb). Therefore, the Nernst potential can be found for every ion. If the voltage difference V across membrane is determined by several different ions the resting membrane potential will be $$V_{ss} = (E_{na}*g_{na} + E_k*g_k + E_{ca}*g_{ca})/(g_{na}+g_k+g_{ca}) \quad (2)$$

Where $g_{na}$, $g_k$, $g_{ca}$ are conductance of Na+, K+, Ca2+

The membrane potential is set by a single ion species with corresponding Nernst potential E. The transmembrane voltage difference $V=V_{in}-V_{ex}$ where $V_{in}$ is intracellular voltage, $V_{ex}$ is extracellular voltage. Let I(t) denote the rate at which positive charge is transferred into the cell across the membrane. I(t) is electrical current. The relationship between current and the rate of charge and voltage is $$C_m(d/dt(V(t))) = I(t) \quad (3)$$

$C_m$ is the capacitance of the membrane. This capacitance shows ability to store a charge on the membrane and depends on geometry of the membrane. The current $I(t)$ is driven by the difference between the membrane voltage and the Nernst potential. According to the Ohm's law $$I(t)=g(E-V(t)) \quad (4)$$

From (3) and (4)

$$C_m(d/dt(V(t)))=g(E-V(t)) \quad (5)$$

The solution of this differential equation with initial voltage $V_0$ is $$V(t)=E-(\exp(-g/C_m)t)(E-V_0)$$

$V(t)$ relaxes exponentially to the resting potential E. The rate of relaxation is dictated by the capacitance C and the conductance g.

The membrane potential is set by multiple ions species. Each ionic current contributes to changes in membrane potential and the ion's individual Nernst potential. Suppose that Na+, K+, Cl− are responsible for setting the membrane potential. Then equation (5) involves three separated currents.

$$C_m(d/dt(V(t)))=I_{na}(t)+I_k(t)+I_{cl}(t) \quad (6)$$

Where each ion-specific current is driven by the difference between the membrane potential and the ion's Nernst potential $$I_{na}(t)=g_{na}(E_{na}-V(t))I_k(t)=g_k(E_k-V(t))I_{cl}(t)=g_{cl}(E_{cl}-V(t)) \quad (7)$$

Where $g_{na}$, $g_k$, $g_{cl}$ are ion-specific membrane conductance or $$C_m(d/dt(V(t)))=g_{na}(E_{na}-V(t))+g_k(E_k-V(t))+g_{cl}(E_{cl}-V(t)) \quad (8).$$

$V(t)$ decays exponentially to rest at rate $\exp(-gt/C_m)$ where $gt=g_{na}+g_k+g_{cl}$.

The polarity of $E_k$, $E_{na}$, $E_{cl}$ depend on the direction of current which rely on the concentration of ions inside and outside cell.

In one model, all cell g-conductivities are dependent on voltage potential V and fixed to a constant value. In a more realistic model, a cell membrane has ion channels dependent on voltage potential V (voltage-gated channels). Every ion channel can adopt two conformations: open and closed. Let O denote to be the open conformation, and C to be the closed. It is described as $$C \leftrightarrow k_1, k_2 \leftrightarrow O$$

Where rate 'constants' k1 and k2 depend on the membrane voltage V. To describe a population of channels, n(t) denote the fraction of channels in the open state at time t. The fraction in the closed state is then 1−n(t), so the next equation is as follows $$(d/dt(n(t))=k_1(V)(1-n(t))-k_2(V)n(t) \quad (9)$$

For a fixed voltage V, steady state $n_{ss}$
$n_{ss}=n_{\overline{\omega}}(V)=k_1(V)/(k_1(V)+k_2(V))$, $n_{ss}=n_{\overline{\omega}}$, equation (9) can be re-written $$(d/dt(n(t))=(n_{\overline{\omega}}(V)-n(t))/\tau(V) \quad (10)$$

$\tau(V)=1/(k_1(V)+k_2(V))$ is the time constant for convergence of the channel population to its steady state. For each ion, the conductance of the membrane is proportional to the number of channels that are open. And conductance for ion could be expressed $$g_i(t)=\overline{g}_i(n(t)) \quad (11)$$

where $\overline{g}_i$ is maximum conductance. Every cell membrane has numerous ion channels through which different types of ions can go through. Some of the channels work as ion pumps to maintain concentration gradient for ions, for instance, with [Ca2+] high in the extracellular space and [K+] high in the cell. Because microcirculation is primarily related to calcium ions Ca2+, the primary focus is on calcium channels in the cell membrane. The ion channels are described using the following formulas. M represents the fraction of Ca2+ channels and ω fraction of open K+ channels with $m_{\overline{\omega}}(V)$, $\omega_m(V)$, $\tau_m(V)$ and $\tau_\omega(V)$ the corresponding steady state time constants as in eq. (10). Following eq. (8) and eq. (11)

$$C_m(d/dt(V(t)))=\overline{g}_{ca}*m(t)(E_{ca}-V(t))+\overline{g}_k*\omega(t)(E_k-V(t))$$

$$Ca2+channels:(d/dt(m(t))=(m_{\overline{\omega}}(V(t)-m(t))/\tau_m(V(t))$$

$$K+channel:(d/dt(\omega(t))=(\omega_{\overline{\omega}}(V(t)-\omega(t))/\tau_\omega(V(t))$$

Where $\overline{g}_{ca}$, $\overline{g}_k$ are maximal membrane conductance. From experimental observation, the calcium channels relax to steady state much more quickly than the potassium channels (i.e. $\tau_m(V) \ll \tau_\omega(V)$, using this fact, $m(t)=m_{ss}(t)=m_{\overline{\omega}}(V(t))$, and for further simplification [27] $\tau_\omega$ is constant.

The present model of the cell membrane includes two other sources of current. The first source of current is non-specific 'leak' current, which describes the background activity of other ion fluxes. This current is driven by the leak Nernst potential, E leak, with fixed conductance g leak. The second additional current source is an applied current, I applied, which describes any current injected into the cell through an external source, or generated from other cells, then $$C_m(d/dt(V(t)))=\overline{g}_{ca}*m(t)(E_{ca}-V(t))+\overline{g}_k*\omega(t)(E_k-V(t))+g_{leek}(E_{leak}-V(t))+I_{applied} \quad (12)$$

In this model of channels, sustained oscillation of membrane voltage may be induced starting from certain levels of induced applied current (Iapplied ~150 pA/cm2). This oscillation may initiate oscillation of the Ca2+ concentration inside the cell. This is a necessary condition for vasomotion and microcirculation. Steady-state behavior is observed for low applied current (Iapplied ~20 pA/cm2) or very high applied currents (Iapplied ~400 pA/cm2). For intermediate values (Iapplied ~150 pA/cm2) the applied current causes continual excitation, resulting in sustained oscillations. Application of a certain current can trigger membrane voltage oscillation to cause the fluctuation of Ca2+ concentration through the cell membrane. This oscillation of the membrane voltage at a certain application of the desired current is associated with resonance in the cells. At different step-levels and timing of the applied current, the membrane voltage varies in different ways: from oscillation with changing frequency to a mixture of response voltage as summation of exponential and sinusoidal signals together, or as signals with burst modes and more. Microcirculation takes place in the micro size capillaries of the blood vessel network. This is believed to be analogous between the neurons cell network and the very small blood vessel network. The nature and response of the respective cells are similar. Small current applications can evoke large membrane voltage oscillations initiating intrinsic electrical-like resonance.

It is submitted that the present invention increases ion migration through cell membrane in the living tissue when several adjustable parameters are used. The higher migration of ions induces higher metabolism, higher consumptions of oxygen, and higher microcirculation of blood. This enhancement of ion migration causes the enhancement of the blood microcirculation by means of applying current into the target membrane using an external alternating magnetic field.

Figure 4A:
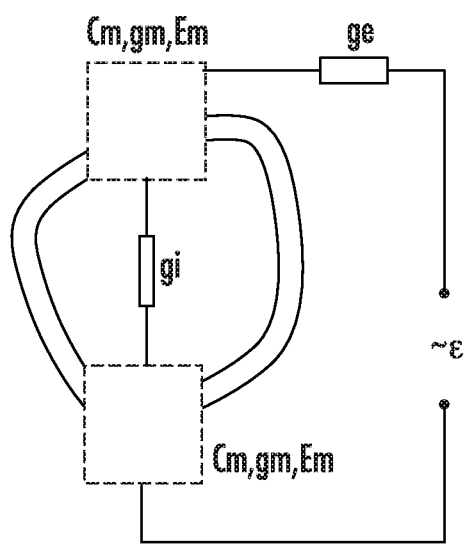
FIG. 4 is illustrative of the target cell membrane and arrangement of the electrical elements and equivalent electrical circuit.
Figure 4B:
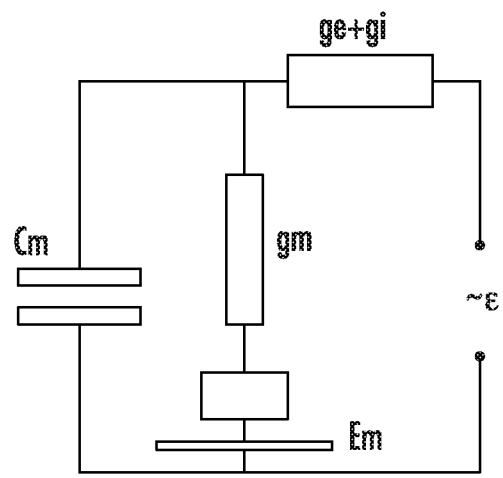

The increased microcirculation depends on the oscillation of ions through the targeted cell membrane. The oscillation can be realized by applying alternating external magnetic field inducing current to the targeted area in the cells. FIG. 4 represents the cell and possible arrangement of the electrical elements of the equivalent electrical circuit B. ε is induced electric field by applying external magnetic field, $C_m$, $g_m$, $E_m$ are capacitance, conductance, and electrical Nernst potential of the membrane; $g_i$ and ge are conductance of the inside and outside cell. According to Kirkoff's law from electrical circuit theory $$C_m(d/dt(V(t))) = g_m(E_m - V(t)) + (g_e + g_i)(V(t) - \varepsilon) \quad (13)$$

The applied current Iadd=$(g_e + g_i)(V(t) - \varepsilon)$ is proportional to the induced electric field E. From electromagnetic theory $$\varepsilon = -(d\Phi/dt) \quad (14)$$

where Φ is a magnetic flux and Φ=SB. Here B is magnetic induction covering area S.

The magnetic induction can be created by the coupled magnetic coils, shown as the Helmholtz coils. The Z-component of this magnetic induction produced by the Helmholtz coils is precisely equal to $$B_z = (\mu_0 N I r^2/2)(1/(z^2 + r^2)^{3/2} + 1/((d-z)^2 + r^2)^{3/2} \quad (15)$$

Where $\mu_0$ is the magnetic permeability, $\mu_0 = 4\pi 10^{-7}$ H/m (Henry/meter), I is current in the coil (Amper), d, coil separation, meters, z, distance along common axis, meters, r, coil radius, meters, N, number of turns (same for each coil). Using (14) and (15)

$$\varepsilon = (d/dt(I))G(N,r,S,d) \quad (16)$$

G(N,r,S,d) is a geometrical factor of the Helmholtz coils. To induce a current $I_{add}$ into the cell electric circuit, the coil current $I_{coil}$ is preferably a periodic triangular function of time. The faster rate dI/dt the bigger tilt on the dependence I(t) and the bigger the applied current into the cell. B is proportional to the current $I_{coil}$ (see equation 15).

As microcirculation improves, the oxygenation of tissue also increases. By applying different levels of applied current into the cell membrane it is possible to find the 'resonance' of the cell system where oscillation of ions through cell membrane will maximize the oxygenation of the tissue. Different rates in time of the coil current (frequency) $I_{coil}$, gives certain applied current into the cell membrane, $I_{add}$. At the same time, one can identify the oxygenation level of the target area where the magnetic field is applied. The oxygenation level can be defined using a Giant Magnetoresistance Sensor (GMS) or Laser Doppler Flow Meter Sensor (LDS). For Helmholtz coils with configuration d=r at the center of the test volume (i.e. z=r/2) the equation (15) can be simplified $$B = (8.99 \times 10^{-7}) NI/r \quad (17)$$

So if N=100; r=0.1 m; $I_{coil}$=1A; S~r×r~0.01 m²; B=1000 microTesla; d($I_{coil}$)/dt~0.1 A/1 second=0.1; ε~$10^{-7}$ Volt; $g_m$=0.01 milisimence=$10^{-5}$ simence. Estimation of applied current is $I_{add}$=V$g_m$~$10^{-11}$=10 picoAmper. With rate d$I_{coil}$/dt=10 A/s the $I_{add}$ will be about 1000 picoAmper.

By varying the current amplitude and current time rate in the coils, or frequency, one can determine the applied current into the cell membrane and at the same time measure oxygenation of the human tissue. The maximum oxygenation is found at a certain applied current where the 'resonance' will appear. The size and density of target cells is different from one organ to another and from one person to another. The resonance of the applied current will therefore be different from person to person or tissue to tissue. Therefore, the first step in any treatment will be to find the "personal resonance of applied current" for the target tissue of the patient. The second step is to apply this preferred applied current to increase the microcirculation in the targeted part of human tissue.

To increase blood microcirculation in tissue, the pairs of Helmholtz coils are built having sufficient size to surround the target tissue. The applied current into the cell membrane is induced by applying the triangle shape alternating magnetic field with coil current from 0.1 A to 1 A and frequency from 18 Hz to 38 Hz. A sensor-Giant Magnetoresistance Sensor (GMS) is used to determine a feedback from the target tissue where the magnetic field is applied. The procedure of applying this range of the magnetic field is recorded and processed to determine "personal resonance applied current" and optimize the blood microcirculation. This procedure includes following steps.

Figure 3:
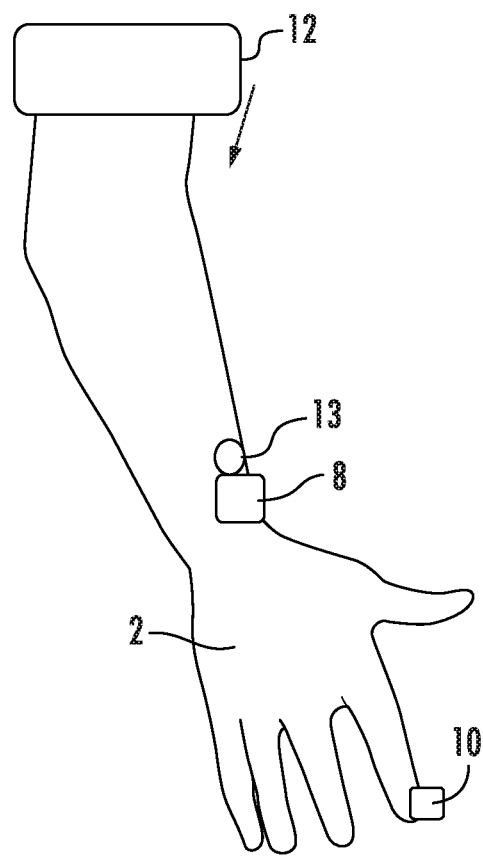
FIG. 3 is illustrative of the setup for the calibration of the GM sensor and LD sensor.
Figure 5:
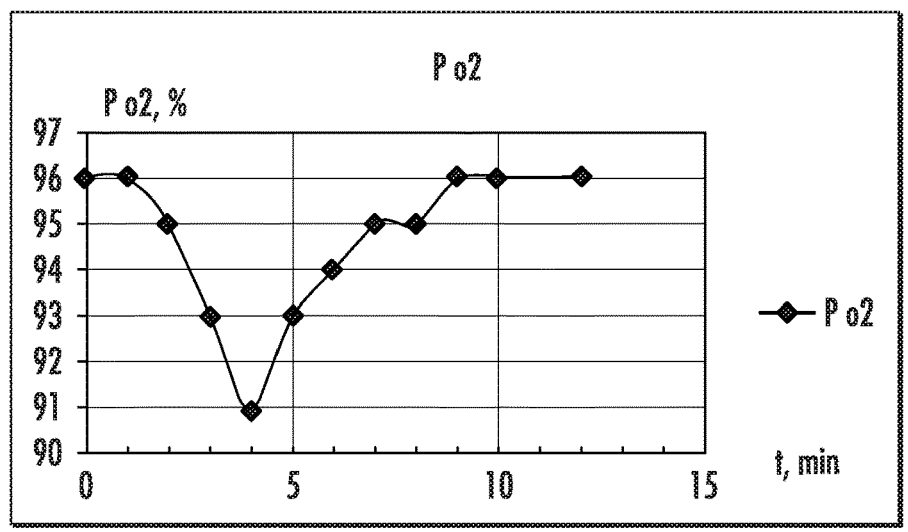
FIG. 5 is illustrative of the calibration of the GMS and LD sensors.
Figure 5:
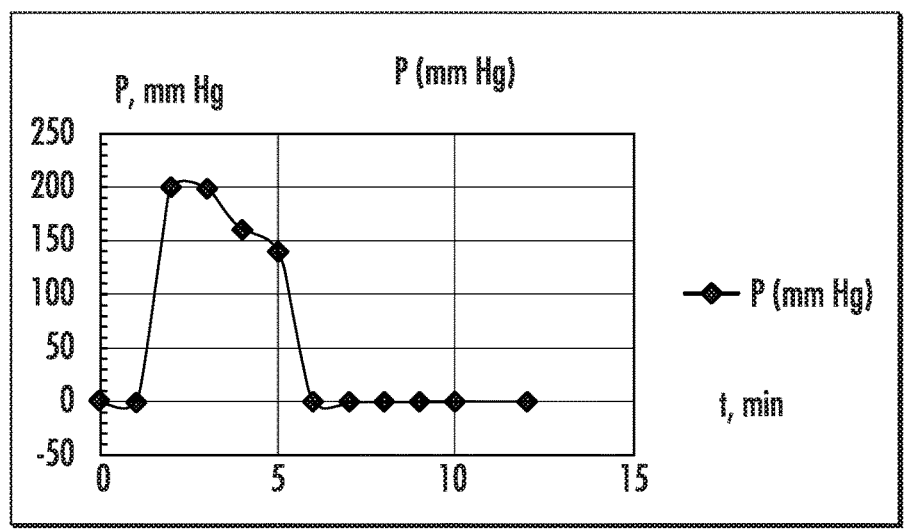
Figure 5:
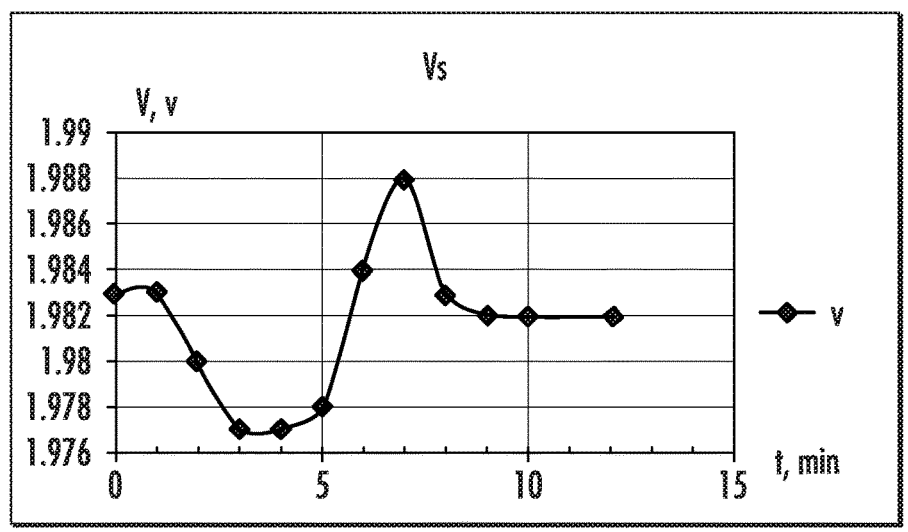

The first step is a calibration step where the components are arranged as shown in FIG. 3 when the target tissue is the palm 2 of a patient. A pressure cuff 12 is attached to the arm, and the feedback sensors GMS 8 and a laser Doppler sensor (LDS) 10 are positioned on the appropriate area of the arm to monitor and control blood microcirculation. The data from the sensors is read as Vs at zero external magnetic field. The pressure is increased pressure cuff 12 up to about 200 mm Hg. This pressure is maintained for approximately two minutes. The pressure is reduced slowly in the cuff at the same time as data is collected from the sensors 8 and 10 as Vs. This reading reflects the increase or decrease of the blood microcirculation in the target tissue of the body part as shown in FIG. 5.

Figure 6:
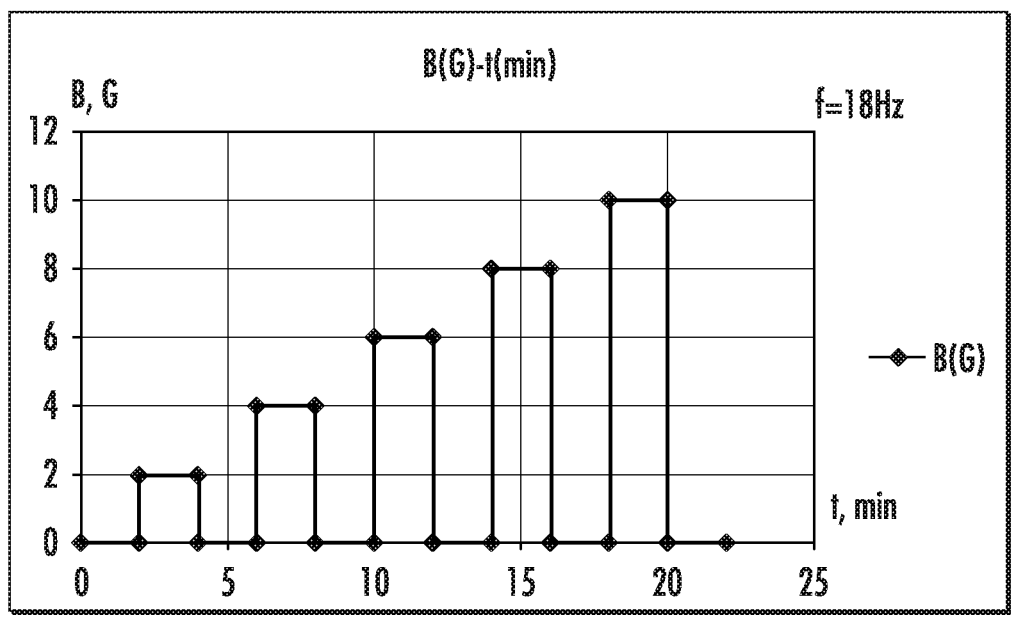
FIG. 6 is illustrative of the time protocol for the external magnetic field; Dependence of the magnetic field vs time and dependence of the GMS signal vs time.
Figure 6:
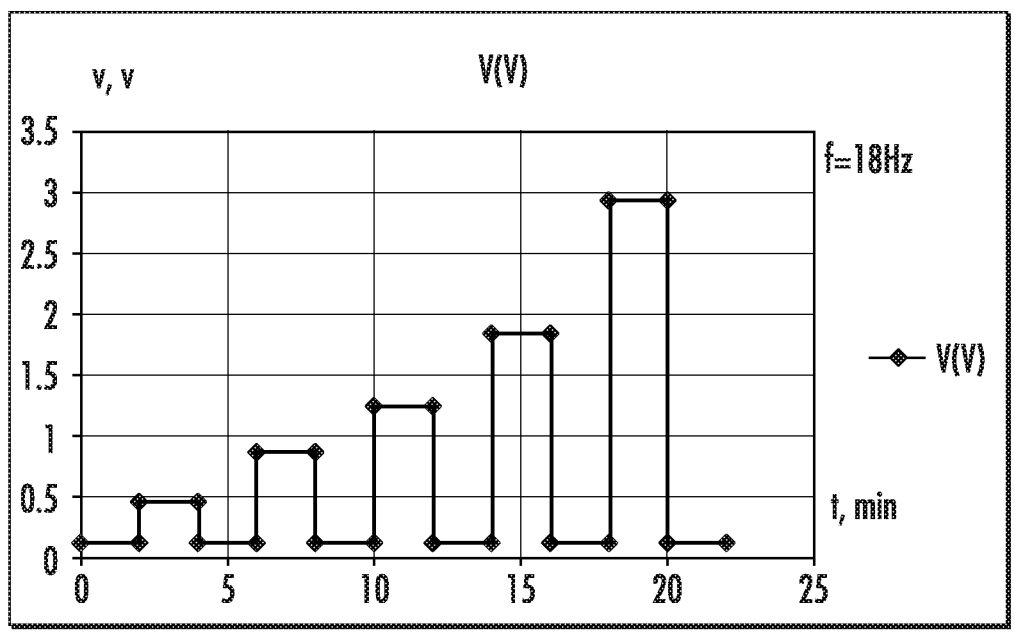

The second step is to determine the time protocol for the applied current from the external magnetic field. The targeted part of human body, for example palm 2 is placed between the Helmholtz coils 4 and 6. A pair of feedback sensors, GMS 8 and LDS 10, are placed in the appropriate area of the arm to sense blood microcirculation. A small permanent magnet 13 is also used to maintain the GMS sensor in the linear area of dependence which relates to the external magnetic field versus the signal Vs from the sensor 8. Initially, when the current through the coil is zero Ampere, the voltage value Vo is established. The data from the GMS sensor 8 (Vs) is read and an applied current to the target tissue is provided by the magnetic coils as shown in FIG. 6. The magnetic coils preferably apply a current with the triangle shape having a frequency of about 18 Hz and an amplitude approximately 0.1 A for a predetermined time, such as two minutes. The next step is to reduce the magnetic field to zero; the magnetic field is maintained at zero for a predetermined time such as two minutes while the data is read from the sensors V(rem), to determine the remnant voltage of the target tissue. Therefore, V(rem) is the remnant voltage in the target tissue after the external magnetic field was applied during two minutes and reduced to zero. The next step is to apply a coil current of about 0.2 A to the coil for about 2 minutes and then reducing the current to zero. The applied current is then kept at zero current for two minutes while at the same time data is read from the sensors V(rem). This procedure is continued by increasing the applied current using stepped increases by about 0.1 A followed by a data collection period where zero current is applied. Finally, the data is presented as the current magnetic field inside the Helmholtz coil as a function of time and the voltage Vs as a function of time as shown in FIG. 5. This time protocol is performed for any frequency to optimize the magnetic field for the blood microcirculation of the target tissue.

The third step is to determine extremes at difference V0−Vs(rem) as a function of the applied magnetic field B, or the current of the magnetic coil $I_{coil}$ at a certain frequency of the external field. The positive difference V0−Vs(rem) indicates a deficiency of the oxygen level. The negative difference indicates an enhancement of the oxygen level which follows from the calibration curve as shown in FIG. 5 showing the graph Vs vs time. The similar time protocol may be done for any frequency and amplitude of the magnetic field depending on the location and type of target tissue. Therefore, as the user proceeds through each of the desired frequencies and amplitudes, the optimum frequency and amplitude of the magnetic field may be determined to effectively increase the blood microcirculation of the target tissue.

An example of the present invention is described herein wherein the palm of a patient was examined to determine the optimal application of the magnetic field to the target tissue. In this example, the palm 2 of the patient was placed between the two Helmholtz coils, 4 and 6. The Helmholtz coils in this embodiment, 4 and 6, preferably include an internal diameter of about 0.05 m, an external diameter of about 0.15 m and a distance between the coils of about 0.05 m. The GM sensor was attached outside these coils to an appropriate area of the arm together with a permanent small magnet located within about 0.015 m from the sensor. The location of the sensor is close to a major blood vessel with oxygenated blood. In this example, the major blood vessel is the radial artery near the palm arch. It is anticipated that the size and location of the Helmholtz coils, 4 and 6, as well as sensors, 8 and 10 may vary depending on the location and size of the target tissue. The sensor's flow data is collected via computer 14 and the signal from the sensor can be seen on the virtual oscilloscope display 16 when the current goes through the coils. At the same time, one can read the root mean square (rms) signal from the computer which is associated with Vs, V0, Vs(rem). The data flow through the computer includes sets of V0, Vs, Vs(rem) for different frequencies fn and amplitudes Hm of the magnetic field, where n, m indexes belong to certain frequencies and amplitudes. Each couple of fn and Hm have V0, Vs(rem) and then the matrix of difference.

In this example, [V0−Vs(rem)] nm has the minimum and maximum which will indicate a more efficient coupling of fn and Hm for more effective treatment of the alternating magnetic field. With the present example, below is the flow of the data at frequency from 18 Hz to 38 Hz and a current through the coils, 0.1, 0.2, 0.3, 0.4, 0.5 A with the coil at a constant G=20 Gauss/Ampere. The position of the palm 2 must be fixed to keep V0 constant at the same level. The earth magnetic field varies from 0.3 to 0.7 Gauss. The GM sensor 8 is very sensitive to the magnetic field (0.004 Gauss is equal 1 mV), which depends on the orientation of the sensor. The data flow table is given below. The first column is the real time in minutes. The second column is the effective current through the coil. The coil constant is A=20 Gauss/Ampere. The third column represents the rms signal from the sensor Vs. The sensor is located outside the coil but still 'senses' the magnetic field. When the current through the coil is zero, the signal Vs(rem) indicates the magnetic properties of the target tissue through the sensor. The fourth column represents the difference between V0 and Vs(rem). If the fourth column is positive, there is a deficiency of the oxygen in the blood vessel; if it is negative, there is an enrichment of the oxygen in the blood vessel. This number indicates which frequency and amplitude of the magnetic field is more efficient for blood microcirculation. The minimum differences for V0 and Vs(rem) at different frequencies f and the current through the coil (magnetic field B) provide direction for the positive application of magnetic therapy. In this device, the frequencies where V0−Vs(rem) is negative provide an indication of the desired frequency and magnetic field for the optimal treatment of the target tissue. As shown in the tables below, the frequencies of 30, 32 and 38 Hertz illustrate the appropriate frequency for the treatment of the target tissue. Similarly, where f=20 Hz and I=0.5 A (10 Gauss) V0−Vs(rem)=−16 mV; at 30 Hz and 0.4 A (8 Gauss) V0−Vs(rem)=−15 mV; and at 38 Hertz and 0.2 A (4 Gauss) V0−Vs(rem)=−14 mV. In this example, there are multiple instances of optimal frequencies and magnetic field to optimize the treatment of the target tissue.

| Time min | I, current A | Vs V (18 Hz)) | V0-Vs (rem) mV (18 Hz) |
|---|---|---|---|
| 1 | 0 | 0.133 | 0 |
| 2 | 0 | 0.129 | |
| 3 | 0.1 | 0.451 | |
| 4 | 0.1 | 0.442 | |
| 5 | 0 | 0.125 | |
| 6 | 0 | 0.127 | 6 |
| 7 | 0.2 | 0.878 | |
| 8 | 0.2 | 0.869 | |
| 9 | 0 | 0.136 | |
| 10 | 0 | 0.135 | −2 |
| 11 | 0.3 | 1.255 | |
| 12 | 0.3 | 1.249 | |
| 13 | 0 | 0.127 | |
| 14 | 0 | 0.125 | 8 |
| 15 | 0.4 | 1.856 | |
| 16 | 0.4 | 1.854 | |
| 17 | 0 | 0.121 | |
| 18 | 0 | 0.123 | 10 |
| 19 | 0.5 | 2.933 | |
| 20 | 0.5 | 2.94 | |
| 21 | 0 | 0.143 | |
| 22 | 0 | 0.142 | −9 |

| Time min | I, current A | Vs V (20 Hz)) | V0-Vs (rem) mV (20 Hz) |
|---|---|---|---|
| 1 | 0 | 0.057 | 0 |
| 2 | 0 | 0.058 | |
| 3 | 0.1 | 0.432 | |
| 4 | 0.1 | 0.43 | |
| 5 | 0 | 0.054 | |
| 6 | 0 | 0.054 | 3 |
| 7 | 0.2 | 0.875 | |
| 8 | 0.2 | 0.87 | |
| 9 | 0 | 0.055 | |
| 10 | 0 | 0.054 | 3 |
| 11 | 0.3 | 1.55 | |
| 12 | 0.3 | 1.548 | |
| 13 | 0 | 0.052 | |
| 14 | 0 | 0.053 | 4 |
| 15 | 0.4 | 2.055 | |
| 16 | 0.4 | 2.049 | |
| 17 | 0 | 0.069 | |
| 18 | 0 | 0.07 | −13 |
| 19 | 0.5 | 3.34 | |
| 20 | 0.5 | 3.342 | |
| 21 | 0 | 0.072 | |
| 22 | 0 | 0.073 | −16 |

| Time min | I, current A | Vs V (22 Hz) | V0-Vs (rem) mV (22 Hz) |
|---|---|---|---|
| 1 | 0 | 0.26 | 0 |
| 2 | 0 | 0.262 | |
| 3 | 0.1 | 0.61 | |
| 4 | 0.1 | 0.601 | |
| 5 | 0 | 0.267 | |
| 6 | 0 | 0.265 | −5 |
| 7 | 0.2 | 1.41 | |
| 8 | 0.2 | 1.41 | |
| 9 | 0 | 0.259 | |
| 10 | 0 | 0.257 | 3 |
| 11 | 0.3 | 2.199 | |
| 12 | 0.3 | 2.18 | |
| 13 | 0 | 0.251 | |
| 14 | 0 | 0.25 | 10 |
| 15 | 0.4 | 2.78 | |
| 16 | 0.4 | 2.778 | |
| 17 | 0 | 0.251 | |
| 18 | 0 | 0.25 | 10 |
| 19 | 0.5 | 3.318 | |
| 20 | 0.5 | 3.312 | |
| 21 | 0 | 0.242 | |
| 22 | 0 | 0.244 | 16 |

| Time min | I, current A | Vs V (24 Hz) | V0-Vs (rem) mV (24 Hz) |
|---|---|---|---|
| 1 | 0 | 0.144 | 0 |
| 2 | 0 | 0.143 | |
| 3 | 0.1 | 0.406 | |
| 4 | 0.1 | 0.401 | |
| 5 | 0 | 0.147 | |
| 6 | 0 | 0.148 | −4 |
| 7 | 0.2 | 1.095 | |
| 8 | 0.2 | 1.081 | |
| 9 | 0 | 0.141 | |
| 10 | 0 | 0.14 | 4 |
| 11 | 0.3 | 1.506 | |
| 12 | 0.3 | 1.511 | |
| 13 | 0 | 0.134 | |
| 14 | 0 | 0.135 | 9 |
| 15 | 0.4 | 2.2 | |
| 16 | 0.4 | 2.21 | |
| 17 | 0 | 0.138 | |
| 18 | 0 | 0.139 | 5 |
| 19 | 0.5 | 2.879 | |
| 20 | 0.5 | 2.87 | |
| 21 | 0 | 0.137 | |
| 22 | 0 | 0.138 | 6 |

| Time min | I, current A | Vs V (26 Hz) | V0-Vs (rem) mV (26 Hz) |
|---|---|---|---|
| 1 | 0 | 0.07 | 0 |
| 2 | 0 | 0.071 | |
| 3 | 0.1 | 0.445 | |
| 4 | 0.1 | 0.44 | |
| 5 | 0 | 0.078 | |
| 6 | 0 | 0.077 | −7 |
| 7 | 0.2 | 0.941 | |
| 8 | 0.2 | 0.939 | |
| 9 | 0 | 0.068 | |
| 10 | 0 | 0.069 | 1 |
| 11 | 0.3 | 1.58 | |
| 12 | 0.3 | 1.57 | |
| 13 | 0 | 0.067 | |
| 14 | 0 | 0.068 | 2 |
| 15 | 0.4 | 2.35 | |
| 16 | 0.4 | 2.31 | |
| 17 | 0 | 0.068 | |
| 18 | 0 | 0.067 | 3 |
| 19 | 0.5 | 2.89 | |
| 20 | 0.5 | 2.891 | |
| 21 | 0 | 0.061 | |
| 22 | 0 | 0.062 | 8 |

| Time min | I, current A | Vs V (28 Hz) | V0-Vs (rem) mV (28 Hz) |
|---|---|---|---|
| 1 | 0 | 0.046 | 0 |
| 2 | 0 | 0.047 | |
| 3 | 0.1 | 0.4 | |
| 4 | 0.1 | 0.41 | |
| 5 | 0 | 0.052 | |
| 6 | 0 | 0.051 | −5 |
| 7 | 0.2 | 0.67 | |
| 8 | 0.2 | 0.668 | |
| 9 | 0 | 0.054 | |
| 10 | 0 | 0.053 | −7 |
| 11 | 0.3 | 1.044 | |
| 12 | 0.3 | 1.04 | |
| 13 | 0 | 0.05 | |
| 14 | 0 | 0.051 | −5 |
| 15 | 0.4 | 1.69 | |
| 16 | 0.4 | 1.692 | |
| 17 | 0 | 0.05 | |
| 18 | 0 | 0.048 | −2 |
| 19 | 0.5 | 2.3 | |
| 20 | 0.5 | 2.31 | |
| 21 | 0 | 0.055 | |
| 22 | 0 | 0.057 | −9 |

| Time min | I, current A | Vs V (30 Hz) | V0-Vs (rem) mV (30 Hz) |
|---|---|---|---|
| 1 | 0 | 0.044 | 0 |
| 2 | 0 | 0.043 | |
| 3 | 0.1 | 0.28 | |
| 4 | 0.1 | 0.279 | |
| 5 | 0 | 0.049 | |
| 6 | 0 | 0.05 | −6 |
| 7 | 0.2 | 0.622 | |
| 8 | 0.2 | 0.62 | |
| 9 | 0 | 0.053 | |
| 10 | 0 | 0.052 | −8 |
| 11 | 0.3 | 1.107 | |
| 12 | 0.3 | 1.078 | |
| 13 | 0 | 0.056 | |
| 14 | 0 | 0.057 | −13 |
| 15 | 0.4 | 1.421 | |
| 16 | 0.4 | 1.425 | |
| 17 | 0 | 0.058 | |
| 18 | 0 | 0.059 | −15 |
| 19 | 0.5 | 2.04 | |
| 20 | 0.5 | 2.029 | |
| 21 | 0 | 0.055 | |
| 22 | 0 | 0.054 | −10 |

| Time min | I, current A | Vs V (32 Hz) | V0-Vs (rem) mV (32 Hz) |
|---|---|---|---|
| 1 | 0 | 0.043 | 0 |
| 2 | 0 | 0.044 | |
| 3 | 0.1 | 0.319 | |
| 4 | 0.1 | 0.309 | |
| 5 | 0 | 0.052 | |
| 6 | 0 | 0.051 | −8 |
| 7 | 0.2 | 0.67 | |
| 8 | 0.2 | 0.671 | |

-continued

| Time min | I, current A | Vs V (32 Hz) | V0-Vs (rem) mV (32 Hz) |
| --- | --- | --- | --- |
| 9 | 0 | 0.047 | |
| 10 | 0 | 0.048 | −5 |
| 11 | 0.3 | 1.15 | |
| 12 | 0.3 | 1.107 | |
| 13 | 0 | 0.048 | |
| 14 | 0 | 0.049 | −6 |
| 15 | 0.4 | 1.47 | |
| 16 | 0.4 | 1.45 | |
| 17 | 0 | 0.046 | |
| 18 | 0 | 0.047 | −4 |
| 19 | 0.5 | 1.89 | |
| 20 | 0.5 | 1.87 | |
| 21 | 0 | 0.049 | |
| 22 | 0 | 0.05 | −7 |

| Time min | I, current A | Vs V (34 Hz) | V0-Vs (rem) mV (34 Hz) |
| --- | --- | --- | --- |
| 1 | 0 | 0.053 | 0 |
| 2 | 0 | 0.054 | |
| 3 | 0.1 | 0.317 | |
| 4 | 0.1 | 0.316 | |
| 5 | 0 | 0.058 | |
| 6 | 0 | 0.059 | −6 |
| 7 | 0.2 | 0.66 | |
| 8 | 0.2 | 0.64 | |
| 9 | 0 | 0.059 | |
| 10 | 0 | 0.06 | −7 |
| 11 | 0.3 | 1.126 | |
| 12 | 0.3 | 1.133 | |
| 13 | 0 | 0.047 | |
| 14 | 0 | 0.048 | 5 |
| 15 | 0.4 | 1.47 | |
| 16 | 0.4 | 1.47 | |
| 17 | 0 | 0.045 | |
| 18 | 0 | 0.045 | 8 |
| 19 | 0.5 | 2.05 | |
| 20 | 0.5 | 2.05 | |
| 21 | 0 | 0.044 | |
| 22 | 0 | 0.045 | 8 |

| Time min | I, current A | Vs V (36 Hz) | V0-Vs (rem) mV (36 Hz) |
| --- | --- | --- | --- |
| 1 | 0 | 0.036 | 0 |
| 2 | 0 | 0.036 | |
| 3 | 0.1 | 0.25 | |
| 4 | 0.1 | 0.25 | |
| 5 | 0 | 0.043 | |
| 6 | 0 | 0.045 | −6 |
| 7 | 0.2 | 0.65 | |
| 8 | 0.2 | 0.61 | |
| 9 | 0 | 0.041 | |
| 10 | 0 | 0.042 | −6 |
| 11 | 0.3 | 1.001 | |
| 12 | 0.3 | 0.96 | |
| 13 | 0 | 0.04 | |
| 14 | 0 | 0.041 | −5 |
| 15 | 0.4 | 1.37 | |
| 16 | 0.4 | 1.371 | |
| 17 | 0 | 0.037 | |
| 18 | 0 | 0.036 | 0 |
| 19 | 0.5 | 1.92 | |
| 20 | 0.5 | 1.91 | |
| 21 | 0 | 0.041 | |
| 22 | 0 | 0.042 | −6 |

| Time min | I, current A | Vs V (38 Hz) | V0-Vs (rem) mV (38 Hz) |
| --- | --- | --- | --- |
| 1 | 0 | 0.036 | 0 |
| 2 | 0 | 0.037 | |
| 3 | 0.1 | 0.27 | |
| 4 | 0.1 | 0.27 | |
| 5 | 0 | 0.04 | |
| 6 | 0 | 0.041 | −5 |
| 7 | 0.2 | 0.487 | |
| 8 | 0.2 | 0.491 | |
| 9 | 0 | 0.038 | |
| 10 | 0 | 0.039 | −3 |
| 11 | 0.3 | 0.8 | |
| 12 | 0.3 | 0.781 | |
| 13 | 0 | 0.039 | |
| 14 | 0 | 0.04 | −4 |
| 15 | 0.4 | 1.275 | |
| 16 | 0.4 | 1.249 | |
| 17 | 0 | 0.039 | |
| 18 | 0 | 0.038 | −2 |
| 19 | 0.5 | 1.75 | |
| 20 | 0.5 | 1.755 | |
| 21 | 0 | 0.041 | |
| 22 | 0 | 0.041 | −5 |

| Time min | I, current A | Vs V (38 Hz) | V0-Vs (rem) mV (38 Hz) |
| --- | --- | --- | --- |
| 1 | 0 | 0.037 | 0 |
| 2 | 0 | 0.037 | |
| 3 | 0.1 | 0.57 | |
| 4 | 0.1 | 0.55 | |
| 5 | 0 | 0.041 | |
| 6 | 0 | 0.043 | −6 |
| 7 | 0.2 | 1.312 | |
| 8 | 0.2 | 1.31 | |
| 9 | 0 | 0.052 | |
| 10 | 0 | 0.051 | −14 |
| 11 | 0.3 | 2.24 | |
| 12 | 0.3 | 2.22 | |
| 13 | 0 | 0.037 | |
| 14 | 0 | 0.038 | −1 |
| 15 | 0.4 | 3.12 | |
| 16 | 0.4 | 3.11 | |
| 17 | 0 | 0.039 | |
| 18 | 0 | 0.038 | −1 |
| 19 | 0.5 | 3.814 | |
| 20 | 0.5 | 3.816 | |
| 21 | 0 | 0.036 | |
| 22 | 0 | 0.037 | 0 |

| Time min | I, current A | Vs V (38 Hz) | V0-Vs (rem) mV (38 Hz) |
| --- | --- | --- | --- |
| 1 | 0 | 0.035 | w/o palmer |
| 2 | 0 | 0.035 | 0 |
| 3 | 0.1 | 0.31 | |
| 4 | 0.1 | 0.31 | |
| 5 | 0 | 0.035 | |
| 6 | 0 | 0.035 | 0 |
| 7 | 0.2 | 0.8 | |
| 8 | 0.2 | 0.77 | |
| 9 | 0 | 0.036 | |
| 10 | 0 | 0.035 | 0 |
| 11 | 0.3 | 1.435 | |
| 12 | 0.3 | 1.425 | |
| 13 | 0 | 0.035 | |
| 14 | 0 | 0.035 | 0 |
| 15 | 0.4 | 2.05 | |
| 16 | 0.4 | 2.02 | |
| 17 | 0 | 0.035 | |
| 18 | 0 | 0.035 | 0 |
| 19 | 0.5 | 2.6 | |

| Time min | I, current A | Vs V (38 Hz)) | V0-Vs (rem) mV (38 Hz) |
|---|---|---|---|
| 20 | 0.5 | 2.58 | |
| 21 | 0 | 0.035 | |
| 22 | 0 | 0.035 | 0 |

External and internal factors may affect this difference V0−Vs(rem). The external factors may include the external temperature, atmospheric pressure, humidity or the existence of the magnetic materials around the target tissue. The internal factors may include the blood pressure, human temperature, concentration of the red blood cells and so on. The time period between the different frequency measurements in this embodiment is around 20 minutes to ensure that the system was adapting to the resting state when the magnetic field is not activated. All sets of measurements were made on the same day. The measurement set for frequency 38 Hz was shown for different days of measurement and indicates the same approach with the negative difference V0−Vs(rem). Additionally, at frequency 38 Hz, the measurement was made without the palm and with the same position of the sensor as for the palm's measurement, the difference V0−Vs(rem) was almost zero at any point. To illustrate the optimal effect of the application of the magnetic field to the target tissue.

The present device is built to determine the optimum blood microcirculation for the target tissue. This device includes the Helmholtz coils 4 and 6 to apply the alternating magnetic field, the giant magnetoresistance sensor 8 to measure feedback after applying the alternating magnetic field, the laser Doppler sensor 10 to measure blood flow, a power amplifier 20 for the Helmholtz coils, the amplifier 22 for the giant magnetoresistance sensor 8, a data acquisition box 24 and virtual function generator 18 and virtual oscilloscope 16 (with a LabView device to create virtual instruments that function as a generator and oscilloscope) which are connected to the computer 14. (see FIG. 1). The Helmholtz coils are the source for the applied current of the magnetic field for enhancement of the blood microcirculation. Any object inside these coils is affected by the magnetic field $B=G(r,d,z)\times I$ where I is the current (A), $G(r,d,z)$ is geometrical function, r is radius of the coils, d is distance between coils, z is variable distance along z axis eq. (15); in our case r=0.05 m, d=0.05 m. and an object is in the center of the coils z=0 m. Outside the coils according to eq. (15), the magnetic field is three times smaller than the magnetic field in the center of the coils.

Figure 2A:
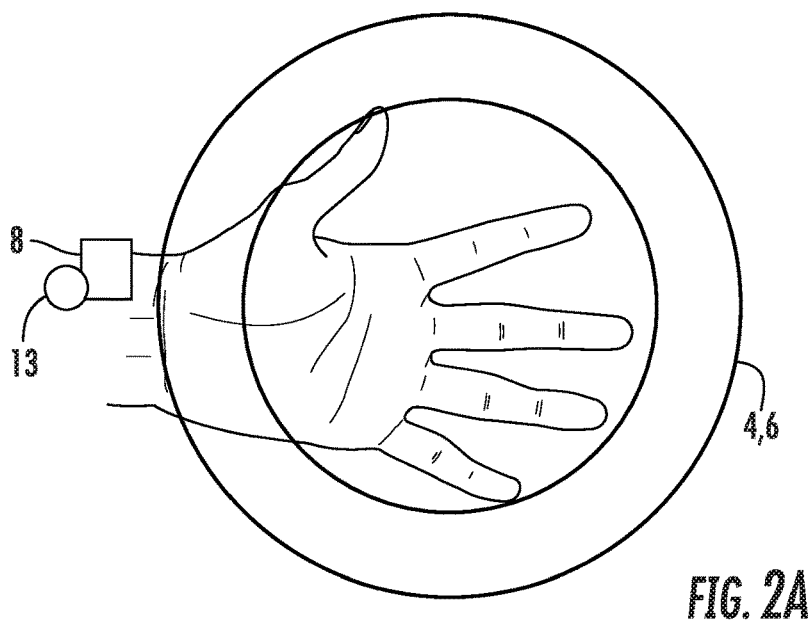
FIG. 2A is illustrative of the top view of the Helmholtz coils and target tissue.
Figure 2B:
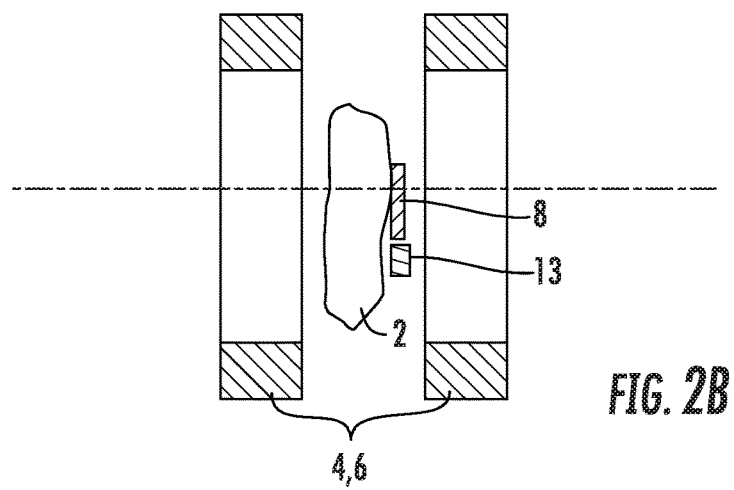
FIG. 2B is illustrative of the side views of the Helmholtz coils and target tissue.
Figure 7:
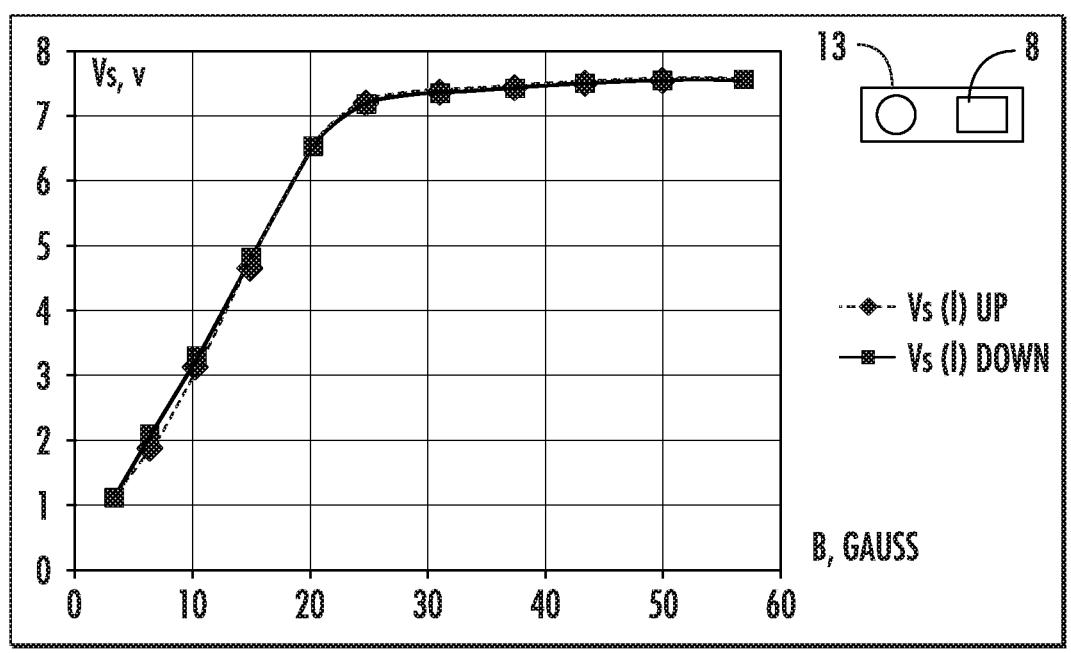
FIG. 7 is illustrative of the GM sensor signal where Vs in the center of the Helmholtz coils as a function of the magnetic field.

Commercially available devices for magnetic field treatment of target tissue do not have sensors to provide an indication of the effectiveness of the treatment. To see the real effect of the magnetic field on influencing the blood microcirculation in the target tissue, the Giant Magnetoresistance Sensor (GMS) 8 was utilized for this purpose (see FIG. 2). An example of a suitable GMS 8 is sensor AAH002 manufactured by NVE Corporation together with an amplifier IN118 manufactured by Texas Instruments. The GMS 8 was put in small magnetic field (~3 G) to use linear dependence of the sensitivity of this sensor Vs (v) as function of the external magnetic field. The arrangement of the small magnet 13 (with an approximate diameter of about 5 mm and a height about 2 mm) and the GM sensor 8 is shown in FIG. 7. The GM sensor 8 is shown in FIGS. 2A and 2B on the top right side where the preferred distance between the small magnet 13 and the sensor 8 is approximately 15 mm. According to the calibration curve using the linear part of this curve, the sensitivity of this sensor S=4 Gauss/v or 1 mV is equal to about 0.004 Gauss. The geomagnetic field is around 0.5 Gauss. Blood can be considered as a magnetic fluid with the red blood cells containing hemoglobin molecules that include a form of the iron oxides. Approximately 40 percent of blood is hemoglobin.

The enhancement of the blood microcirculation under alternating magnetic field has the following sequence: applying magnetic field, inducing additional current through the cell membrane, increasing the usage of oxygen and creating more demand for the hemoglobin. Increasing the hemoglobin in the blood stream changes the magnetic properties of the blood which is then recognized using the GM sensor 8. The sensor measures the magnetic induction B which is $B=\mu_0(H+M)$ where H is the external magnetic field. M, is magnetization of the blood and to is a magnetic constant. Magnetization is proportional to the concentration of the magnetic particles inside fluid, in our case hemoglobin cells. As shown in calibration curves, the sensitivity of the sensor is sufficient to detect small changes in the hemoglobin in the blood.

Each human has specific sets of parameters $g_{Ca}$, $g_K$, $g_l$ and more (see eqs 8-13) which influence the properties of the cell membrane. Every human has a different concentration of the red blood cell particles which vary from about 30 to 40 percent of the blood. This means that every human individual has their own effective range of the value and frequency of the applied magnetic field to obtain effective improvement of the blood microcirculation. Using feedback from the giant magnetoresistance sensor 8, the enhancement of the blood microcirculation will be optimized and the healing effect from the application of the alternating magnetic field will be maximized.

What is claimed is:

1. A method for treating target tissue of a patient, comprising;
   providing a magnetic field generating source to apply a magnetic field to the target tissue of the patient;
   providing a sensor which detects the applied magnetic field in the microcirculation of the target tissue; and
   applying a subsequent magnetic field to the target tissue that is adjusted in response to the detected applied magnetic field in the microcirculation of the target tissue to optimize the treatment of the target tissue of the patient.

2. The method of claim 1 wherein a pair of Helmholtz coils are configured to apply the magnetic field to the microcirculation in the target tissue of a patient.

3. The method of claim 1 wherein the sensor is a giant magnetoresistance sensor to detect the applied magnetic field in microcirculation of the target tissue.

4. The method of claim 1 wherein the applied magnetic field on the target tissue is evaluated by sensing the applied magnetic field in the microcirculation in the target tissue of the patient and the subsequent application of a magnetic field to the target tissue is adjusted to optimize the application of teh magnetic field to the microcirculation of the target tissue.

5. The method of claim 1 wherein a pair of Helmholtz coils are configured to apply the magnetic field to the target tissue of a patient and wherein the sensor is a giant magnetoresistance sensor to detect the applied magnetic field in the microcirculation of the target tissue and the subsequent magnetic field is applied to the target tissue in response to the detected magnetic field in the microcirculation in the target tissue.

6. The method of claim 1 wherein the magnetic field is applied to the target tissue at multiple different frequencies and the magnetic field in the microcirculation is detected for each different frequency to optimize the frequency of the subsequently applied magnetic field.

7. The method of claim 1 wherein the magnetic field is applied to the target tissue at multiple different amplitudes and the magnetic field in the microcirculation is detected for each different amplitude to optimize the subsequently applied magnetic field to the target tissue.

8. The method of claim 1 wherein the magnetic field is applied to the target tissue at multiple different frequencies and amplitudes and the magnetic field in the microcirculation is detected for each different frequency and amplitude to optimise the frequency and amplitude of the subsequently applied magnetic field.

9. The method of claim 1 wherein the sensor allows for the measuring of the remnant applied magnetic field in the microcirculation of the patient, wherein the subsequent magnetic field applied to the target tissue is adjusted in response to the detected remnant applied magnetic field in the microcirculation of the target tissue to optimize the frequency of the subsequently applied magnetic field.

10. A method for treating microcirculation in target tissue of a patient, comprising;
providing a pair of Helmholtz coils as a magnetic field generating source to apply a magnetic field to the target tissue of the patient;
providing a signal recording device to record signals from the giant magnetoresistance sensor; and
applying a subsequent magnetic field by the Helmholtz coils to the target tissue that is adjusted in response to the detected applied magnetic field in the microcirculation of the target tissue to optimize the treatment of the target tissue of the patient.

11. The method of claim 10 including the steps of applying a plurality of magnetic fields to the target tissue and detecting the applied plurality of magnetic fields in the microcirculation of the target tissue following discontinuation of the application of each of the applied magnetic fields and subsequently applying an adjusted magnetic field to optimize an effect of the applied plurality of magnetic fields on the target tissue of the patient.

12. The method of claim 10,
wherein the applied magnetic field is an initial magnetic field, and
further including the steps of applying a plurality of magnetic fields,
detecting teh applied plurality of magnetic fields, comparing the detected initial applied magnetic field with the detected applied plurality of magnetic fields, and subsequently applying an adjusted magnetic field to the target tissue.

13. The method of claim 12 wherein the microcirculation in the target tissue is optimized based on the subsequently applied adjusted magnetic field.

14. The method of claim 10 further including the step of applying the magnetic field over a plurality of frequencies and amplitudes to the target tissue to determine an effect of the magnetic field in the microcirculation of the target tissue and acquiring signals from the giant magnetoresistance sensor of the detected applied magnetic field at the plurality of time periods following the application of the applied magnetic field;
evaluating the signals from the giant magnetoresistance sensor to determine the optimal frequency and amplitude of the applied magnetic field; and
applying an adjusted magnetic field based on the optimal frequency and amplitude of teh applied magnetic field to the target tissue.

* * * * *